United States Patent [19]

Ito et al.

[11] Patent Number: 5,448,998
[45] Date of Patent: Sep. 12, 1995

[54] METHOD OF MEASURING A SUBJECT'S PHYSICAL STRENGTH AND APPARATUS THREFOR

[75] Inventors: Masao Ito; Masaaki Mizuno; Terumi Ishiguro, all of Tokyo, Japan

[73] Assignee: Combi Corporation, Tokyo, Japan

[21] Appl. No.: 127,599

[22] Filed: Sep. 28, 1993

[30] Foreign Application Priority Data

Sep. 29, 1992 [JP] Japan .................. 4-259655

[51] Int. Cl.$^6$ ......................................... A61B 5/0205
[52] U.S. Cl. ...................... 128/718; 128/707
[58] Field of Search ............... 128/671, 668, 670, 707, 128/716, 719, 700, 706, 691; 482/900

[56] References Cited

U.S. PATENT DOCUMENTS

| | | | |
|---|---|---|---|
| 4,566,461 | 1/1986 | Lubell et al. ............... | 128/668 |
| 4,678,182 | 7/1987 | Nakao et al. ............... | 482/63 |
| 5,158,093 | 10/1992 | Shvartz et al. ............... | 128/668 |
| 5,230,673 | 7/1993 | Maeyama et al. ............... | 482/900 |

FOREIGN PATENT DOCUMENTS 142694  9/1989  Japan .
426413  1/1992  Japan .

OTHER PUBLICATIONS

"Practical Side of Exercise Cure," Apr. 15, 1991, p. 5.
"Introduction to Exercise Physiology," Apr. 20, 1975, pp. 168–173.
"Evaluation of PWC75%HRmax as an Index of Endurance Work Capacity," *Japanese Journal of Sports Sciences*, Jul. 15, 1984, pp. 559–562.

*Primary Examiner*—Lee S. Cohen
*Assistant Examiner*—Brian M. Green
*Attorney, Agent, or Firm*—Sughrue, Mion, Zinn, Macpeak & Seas

[57] ABSTRACT

A method of measuring physical strength of a subject and an apparatus therefor in which the maximum oxygen uptake based on 75% of the estimated maximum heart rate as a reference is estimated to thereby evaluate physical strength based on the oxygen uptake during exercise. The oxygen uptake is used as an index for evaluating physical strength, and VO$_2$@75% HRmax, which is oxygen uptake measured at 75% of estimated maximum heart rate, is used as a reference so that comparison can be made safely with a measured value even for middle and high ages. The apparatus is provided with a load device which can give a ramp load to a subject (e.g. 15 W/min to male and 10 W/min to female), a pulse rate detecting device which can measure pulse rate successively in the duration in which the load is given to the subject, and a device for averaging the measured pulse rate and the value of the given load over small time periods, subjecting the value of the pulse rate relative to the value of the load to straight line regression, and calculating the slope A and offset B of the resulting straight line.

13 Claims, 16 Drawing Sheets

FIG. 5(b)
FIG. 5(a)
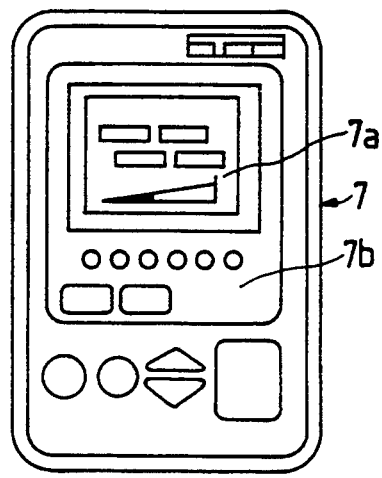
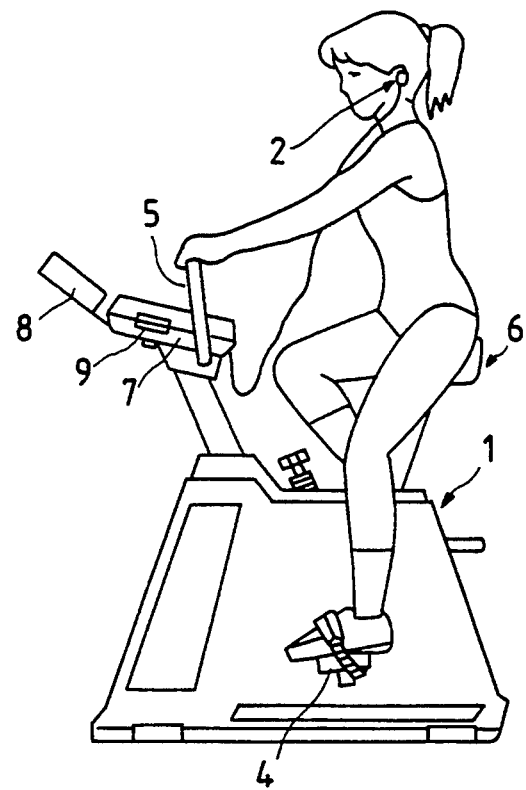

W-HR LINE

W-VO2 LINE

V̇O2 75% @ HRmax ESTIMATED LINE

PHYSICAL STRENGTH EVALUATION TABLE OF MALE BASED ON VO2 @ 75%HRmax n=90

| STRAIGHT LINE OF MALE AVERAGE (REGRESSION) | Y= -10.57261x +1929.8413 |
|---|---|
| +2.0σ | Y= -10.57261x +2613.4967 |
| +1.2σ | Y= -10.57261x +2340.0346 |
| +0.4σ | Y= -10.57261x +2066.5724 |
| -0.4σ | Y= -10.57261x +1793.1102 |
| -1.2σ | Y= -10.57261x +1519.6481 |

PHYSICAL STRENGTH EVALUATION TABLE OF FEMALE BASED ON VO₂ @ 75% HRmax n=80

| STRAIGHT LINE OF FEMALE AVERAGE (REGRESSION) | Y= -3.94734x +1187.4861 |
|---|---|
| +2.0σ | Y= -3.94734x +1573.9355 |
| +1.2σ | Y= -3.94734x +1419.3557 |
| +0.4σ | Y= -3.94734x +1264.7760 |
| -0.4σ | Y= -3.94734x +1110.1962 |
| -1.2σ | Y= -3.94734x +955.61649 |

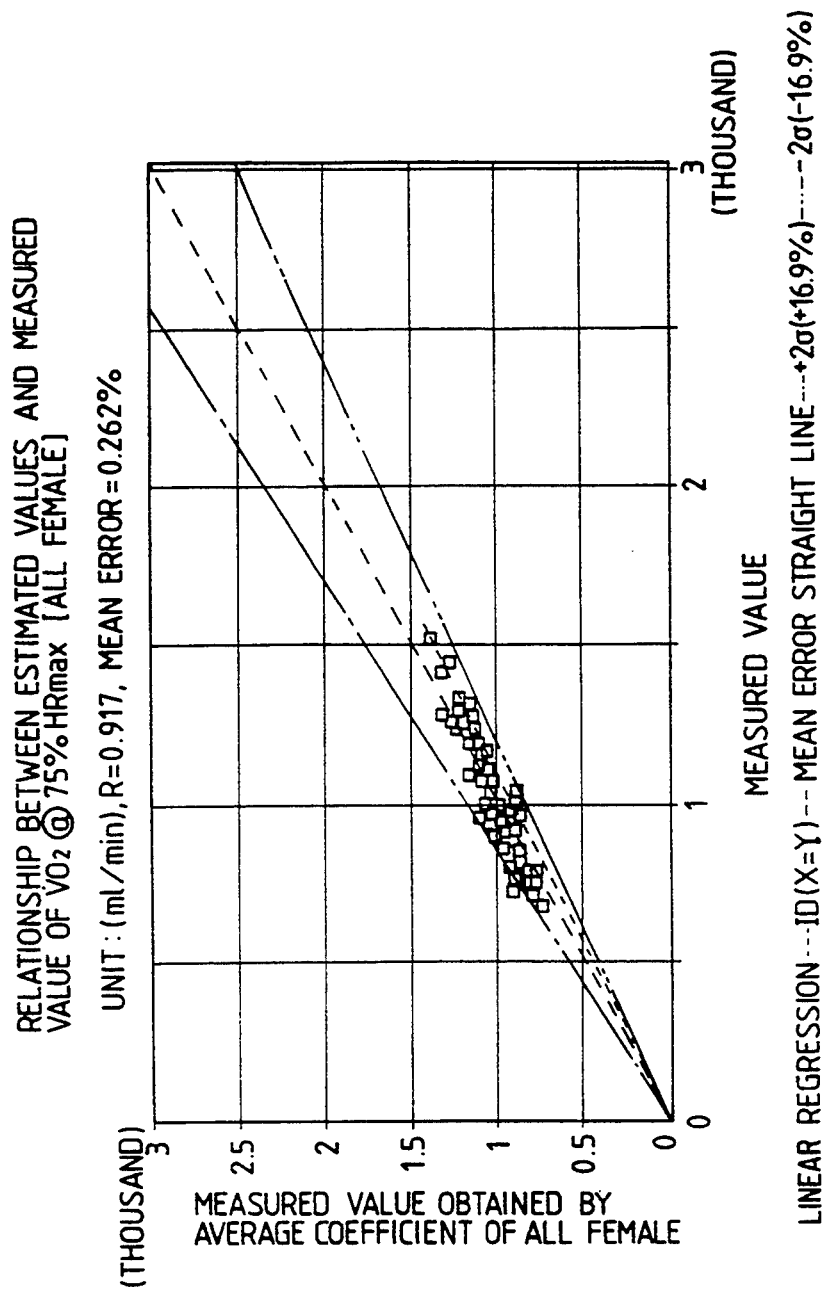

METHOD OF MEASURING A SUBJECT'S PHYSICAL STRENGTH AND APPARATUS THREFOR

BACKGROUND OF THE INVENTION

1. Field of the Invention

The present invention relates to a method of measuring a subject's physical strength and an apparatus therefor in which the oxygen uptake based on 75% HRmax (75% of the patient's maximum heart rate) is estimated so that the physical strength of the subject based on oxygen uptake can be evaluated over a wide range of ages safely and accurately and within a range in which a comparison can be made with other measured values.

This application claims priority from Japanese Patent Application No. Hei 4-259655, the disclosure of which is incorporated herein by reference.

2. Description of the Related Art

Known methods of measuring physical strength, include those in which the power of output by a subject such as PWC75% HR max (load at 75% of maximum heart rate) (Japanese Patent Post-Examination Publication No. Hei-1-42694), PWC170, PWC150, PWC130 or the like, is used for evaluation. Also, a method in which the maximum oxygen uptake is obtained through estimation based on the measurement of physical strength under maximum oxygen uptake so that the measured value of physical strength under maximum oxygen uptake is used for evaluation is known (Japanese Patent Unexamined Publication No. Hei-4-26413).

However, while the former method is easy to apply, it has a disadvantage in that the power, as an evaluation of physical strength, measured by one measuring apparatus cannot be easily converted into the power measured by another measuring apparatus and therefore the power is not good for a general index because the various measuring apparatus are different in efficiency depending on the type thereof (e.g., treadmill, bicycle, ascending stairs, and so on).

The latter method uses the oxygen uptake of a subject as an evaluation so that the difference between different apparatuses is comparatively small and the oxygen uptake can be used as a general index. In order to actually measure the oxygen uptake, however, it is necessary to cause the subject to assume all out and therefore the oxygen uptake is not a good evaluation index for middle aged and older subjects. Further, when a step-like load is used, there are difficulties in that, for example, the load changes suddenly so that the subject's pulse is disturbed and it is difficult to finely adjust the load at the end of exercise.

Further, recently, an aerobic threshold (AT) is used as an index for measuring physical strength since the maximum oxygen uptake method is not entirely safe. However, it is not easy to detect AT. Accordingly, the judgment has been performed based on a plurality of judging factors or various algorithms such as a V-slope method corresponds to an algorithm for automatically detecting a point (for example, an inflection point of $VCO_2/VO_2$, a point where $VE/VO2$ increases suddenly while $VE/VO2$ has no change) and so on. However, currently it is necessary to use more than one of the above criterion in order to make an accurate determination and thus a determination must be made from many points. In addition, a device for analyzing exhalation is expensive.

There remains therefore a question as to whether or not the maximum oxygen uptake is a useful strength index when it is estimated.

SUMMARY OF THE INVENTION

An object of the invention is to solve the foregoing problems. In order to attain this object, in a preferred embodiment the oxygen uptake is used as an index for evaluating physical strength, and $VO_2@75\%$ HRmax which is the oxygen uptake rate measured on the basis of estimated 75% HRmax as a reference so that comparison with a measured value can be made safely even in middle aged and older subjects. Preferably, as an estimated HRmax (maximum heart rate), 209−0.69·age is used for males and 205−0.75·age is used for females. Also, 220− age, or the like can be generally applied to subjects of either sex. Preferably, the apparatus is provided with a load device which applies a ramp load to the subject (15 W/min to male and 10 W/min to female in a preferred embodiment), a pulse rate detecting device which can measure pulse rate constantly while the load is being applied, and a device for averaging the measured pulse rate and the value of the given load over every 10 seconds, and subjecting the data of pulse rate relative to the load to straight line regression to thereby calculate the slope A and offset B of the resulting straight line. The pulse rate detecting device may be replaced by a heart rate detecting device such as an Electrocardiograph, or the like.

Preferably, the same load protocol used for calculating A and B is used for subjects of all ages and the data of oxygen uptake measured relative to a load value for every individual subject is subjected to regression, and average slope C and offset D are determined for each of male and female subjects by averaging the values of the slope C and offset D from the obtained straight lines of regression. The calculation of $VO_2$ (rate of oxygen consumption) is accomplished by using the following expression to estimate aimed $VO_2@75\%$ HRmax (rate of oxygen uptake at 75% of maximum heart rate) from the above-mentioned values A, B, C and D.

$$VO_2 = \frac{C}{A} \cdot HR + \left[ D - \frac{B \cdot C}{A} \right] \quad (1)$$

Further, a method of stepwise evaluating estimated and measured $VO_2@75\%$ HRmax by use of standard deviation for every age, average standard deviation or the like, in order to judge the level of physical strength measured is provided.

The apparatus has a key pad input device through which age, sex, weight and the like are entered, and a display screen such as an LCD, or the like for displaying instructions and output data. Data may be output to a printer, an IC card, an RC232C port, or the like.

According to the present invention, measurement can be performed safely even on subjects of middle and high ages because the measurement is ended at 75% of the estimated maximum heart rate, and the estimated value of oxygen uptake used as an index in a patient for evaluating physical strength is not dependent on the apparatus and thus it can be used for general purpose measurement. Particularly, unlike the measured oxygen uptake, the estimated oxygen uptake can be compared with an actually measured value at any time. Accordingly, the present invention has a merit in that the accuracy of the measuring apparatus can be confirmed. Further, 75% of maximum heart rate is significant in exercise physiology as an upper limit of aerobic exercise (see "Investigation of Propriety of PWC75% HRmax as a Scale of Evaluation of All One's Endurance", J. J. of Sports Sciences, vol. 3, No. 7, pp. 559 to 562, Jul. 15, 1984), and it can be compared in relation to PW75% HRmax evaluation (see Japanese Patent Post—Examination No. Hei-1-42694) which is now widely used.

BRIEF DESCRIPTION OF THE DRAWINGS

FIGS. 5(a) and (b) are explanatory diagrams illustrating an example of an apparatus for measuring physical strength according to the preferred embodiment;

FIG. 19 is a diagram of a relationship between estimated values and measured values of oxygen uptake @75% HRmax of all females measured by using the apparatus for measuring physical strength according to the preferred embodiment.

DETAILED DESCRIPTION OF THE PREFERRED EMBODIMENT

Figure 1:
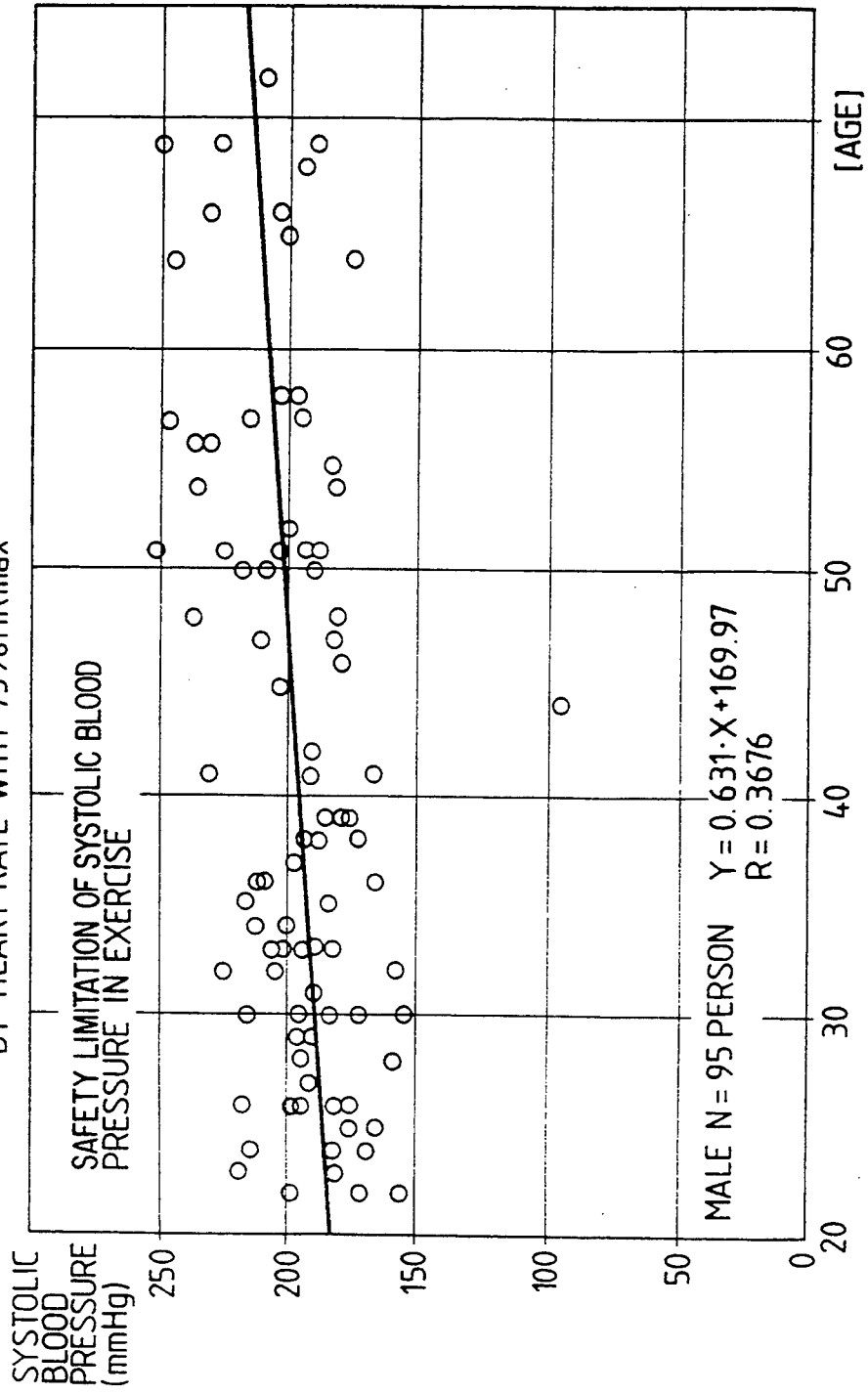
FIG. 1 is a diagram representing data of systolic blood pressure of male subjects by age at the end of exercise, obtained by a measurement method of the preferred embodiment.
Figure 2:
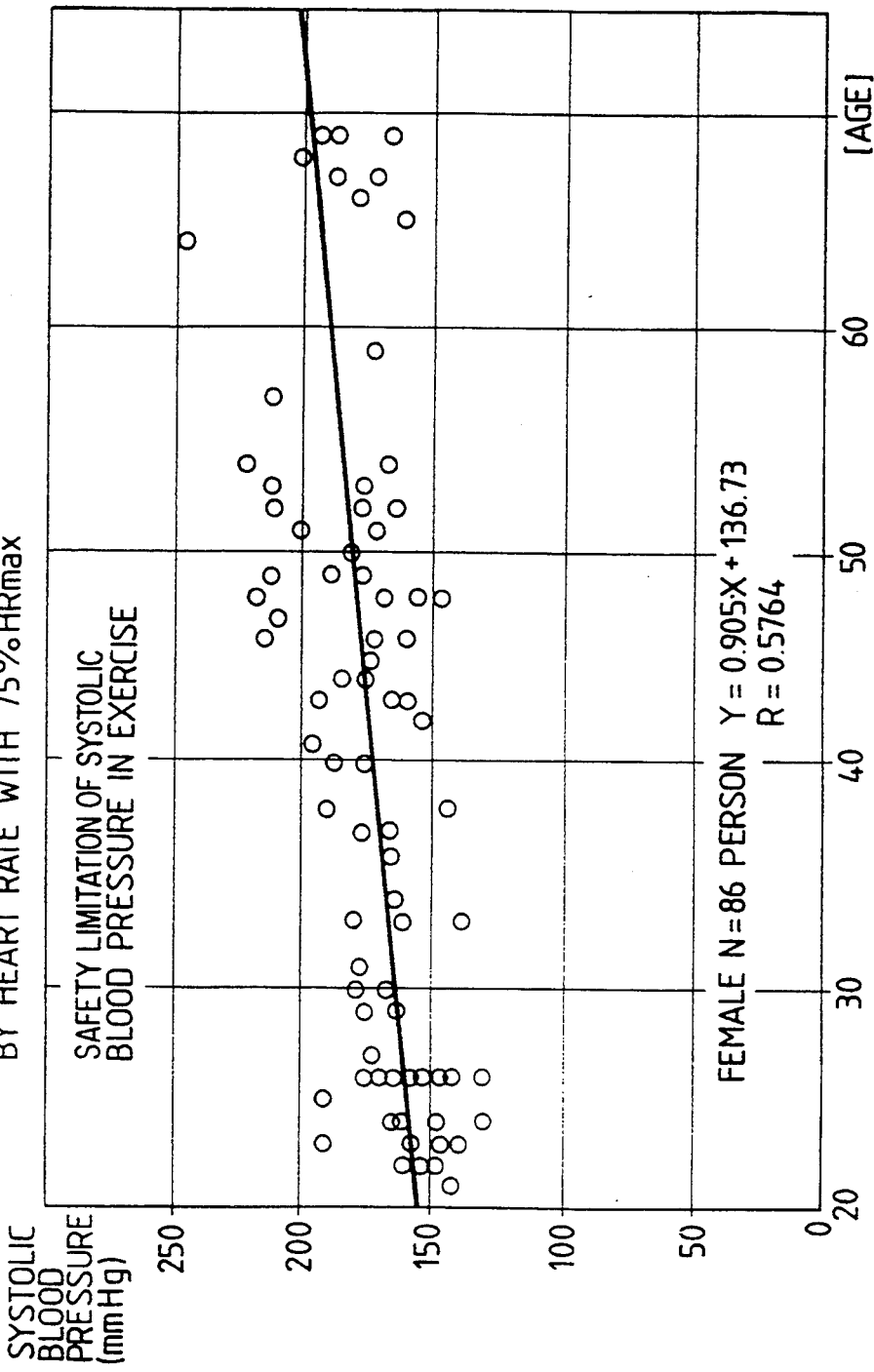
FIG. 2 is a diagram representing data of systolic blood pressure of female patients by age at the end of exercise, obtained by a measurement method of the preferred embodiment.
Figure 3:
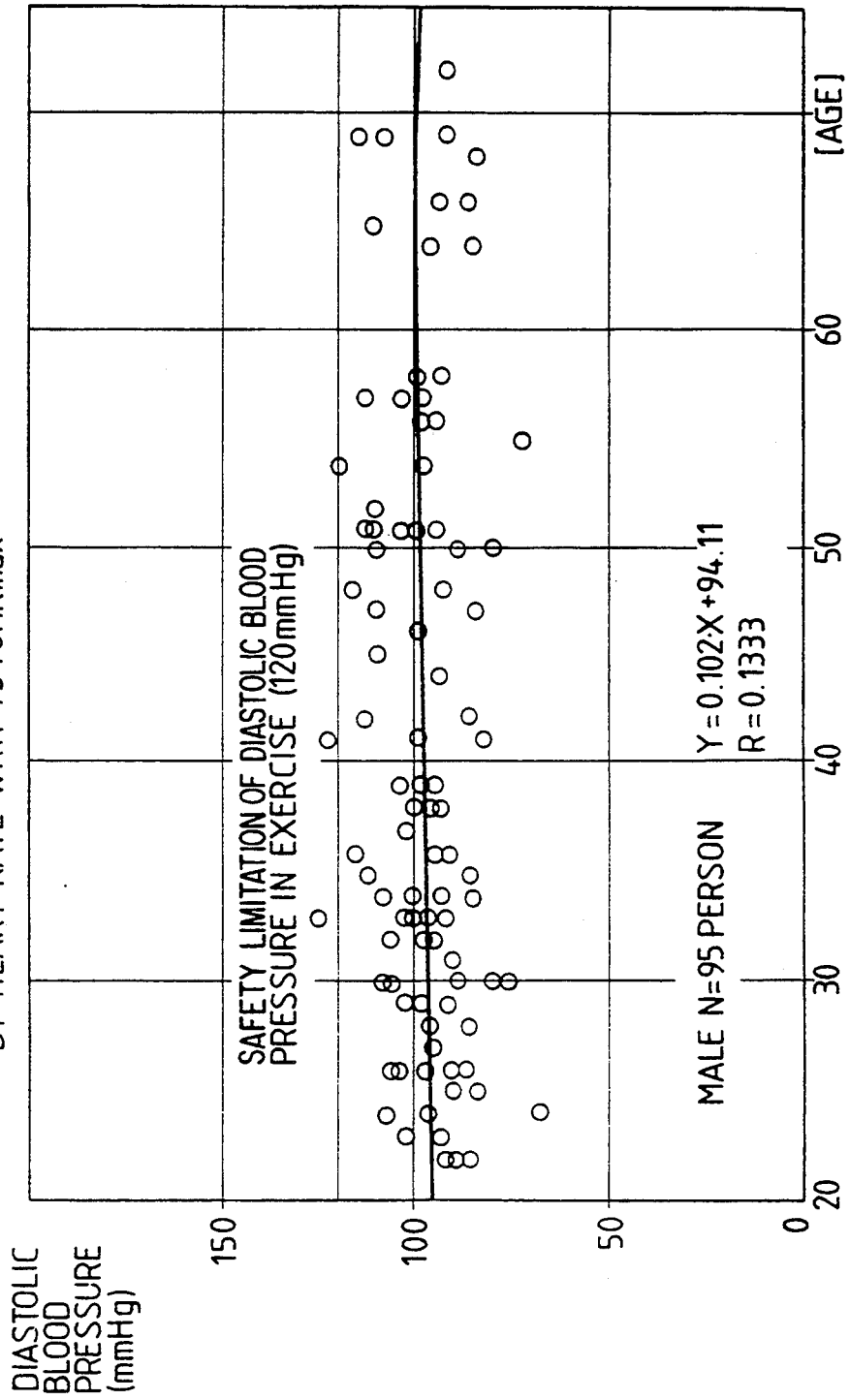
FIG. 3 is a diagram of data representing diastolic blood pressure of male patients by age at the end of exercise, obtained by a measurement method of the preferred embodiment.
Figure 4:
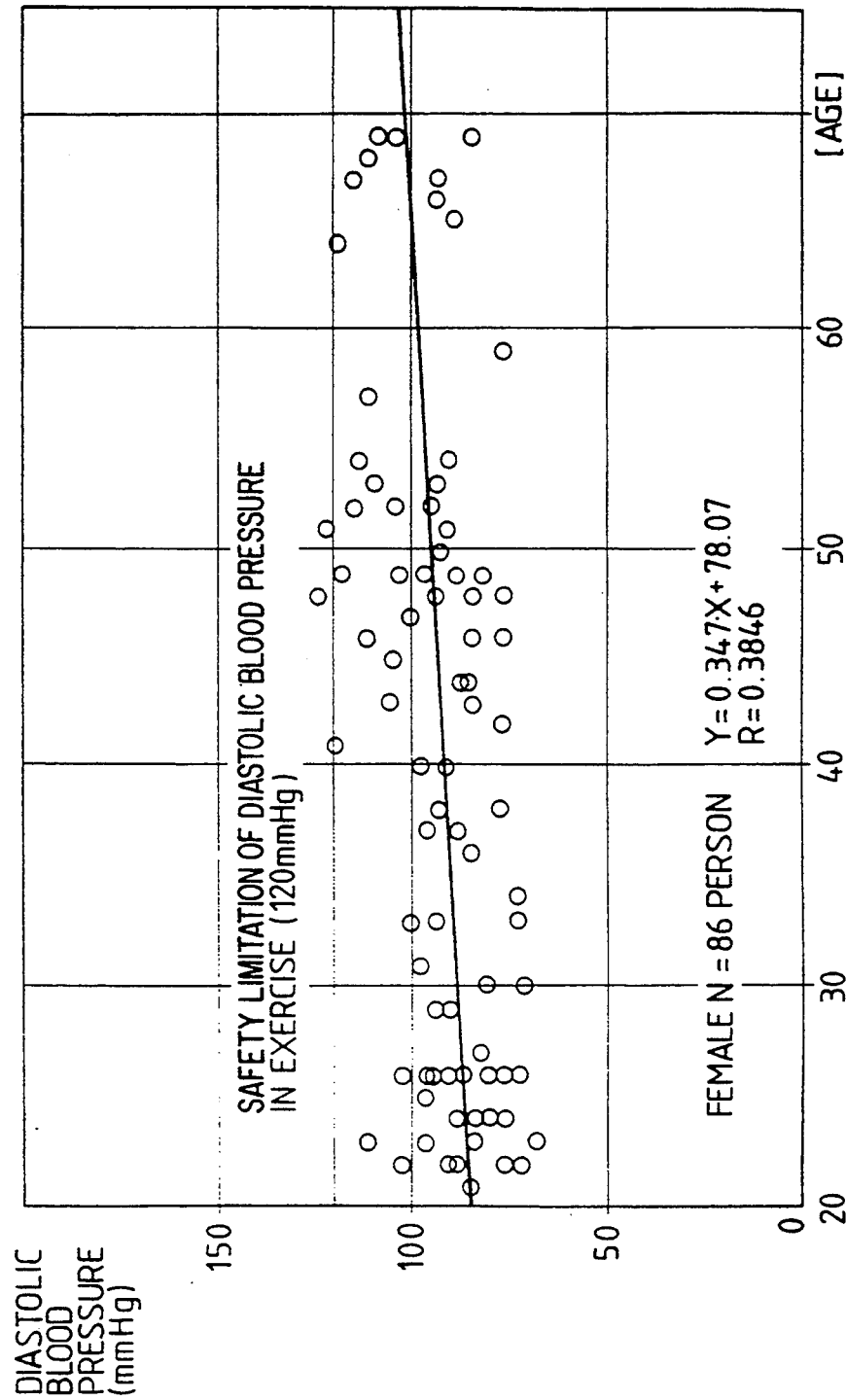
FIG. 4 is a diagram of data representing diastolic blood pressure of female patients by age at the end of exercise, obtained by a measurement method of the preferred embodiment.

Presently, there are various known ways in which a load can be imparted to a subject to obtain the maximum quantity of oxygen consumption through estimation. However, it is difficult to compare various measuring apparatus with each other to judge the ability of estimation of the maximum oxygen uptake in those apparatuses since the maximum oxygen uptake of various patients including those middle aged and older ages must be actually measured in order to perform the comparison. Therefore, most of such apparatus cannot confirm accuracy clearly even if they can make the estimation.

Particularly, although physiological criterion can be used, such as limiting the gas exchange ratio ($VCO_2/VO_2$,) to be less than 1.0, or limiting the oxygen uptake even if a load is increased, ("Introduction to Exercise Physiology", published by Taishukan Shoten, pp. 168 to 173) some subjects must stop exercise due to weakness of their foot muscles before truly testing their endurance. Also, some subjects, particularly middle aged or higher, must stop exercise since their systolic blood pressure reaches 250 mmHg, which is a criterion for stopping, before all-out exercise is obtained ("Practical Side of Exercise Cure", published by Nankodo Shoten, p.5, tables 1 to 10). Finally, some subjects simply stop exercise before reaching a physiological all-out state. Thus the conditions are not always uniform, and it is nearly impossible to increase the accuracy of estimation.

The reason why conventional apparatus cannot be compared with each other is because the accuracy of the apparatus cannot be established because estimated values obtained therein cannot be compared with the measured value easily. In the experiment we conducted upon 181 subjects (male: 95, female: 85) aged from their twenties to their sixties, blood pressure was more important as the condition, for stopping in subjects of higher ages. In connection, in the data of the systolic and diastolic blood pressure at the end of exercise obtained by a method of measuring physical strength according to the present invention, the older a subject is, the closer this data is to the limitation of safety (see FIGS. 1 through 4 which illustrate blood pressures at 75% HRmax). That is, the older a subject is, the more difficult the actual measurement of his maximum oxygen uptake becomes because blood pressure is raised to dangerous levels, and therefore it cannot be said that the maximum oxygen uptake is a practical index. However, as is apparent from the data of FIGS. 1–4, when exercise is stopped at 75% HRmax, most patients have a systolic blood pressure which is well under 250.

An embodiment of the method of measuring physical strength and an apparatus therefor according to a preferred embodiment of the present invention will be described with reference to FIGS. 5 to 19. First, an embodiment of the apparatus for measuring physical strength according to the present invention will be described.

FIGS. 5(a) and 5(b) show the entire apparatus for measuring physical strength according to this embodiment. The apparatus for measuring physical strength is constituted by a bicycle ergometer body 1 and a pulse rate detection sensor 2. The bicycle ergometer body 1 is constituted by a load generating portion which employs an eddy-current brake load device 3, a set of pedals 4, a handle 5, a saddle 6, a control box 7 and a printer 8. The eddy-current brake load device 3 is arranged to generate a load in accordance with an electromagnetic brake system, that is, it produces a ramp load (a load which increases with elapsed time). Preferably, a device that can maintain constant wattage control (even if the number of rotations N of the pedal changes, torque T is controlled to maintain the load $W = N \cdot T$ to be a ramp value) is used as the eddy-current brake load device 3. Accordingly, it is possible to supply a stable load.

The control box 7 is illustrated in detail in FIG. 5(b). A display portion 7a constituted by an LCD screen, displays "Pulse", "Number of Rotations" of the pedal, and the state of the "Load" in the upper portion thereof. A plurality of function keys 7b for selecting "Load", "Age", "Weight" and "Sex" are provided in the lower portion of the display portion 7a. Measured data is printed by the printer 8, and can also be stored in a memory card 9 or the like. Also, data can be input from a memory card, or the like.

Figure 6:
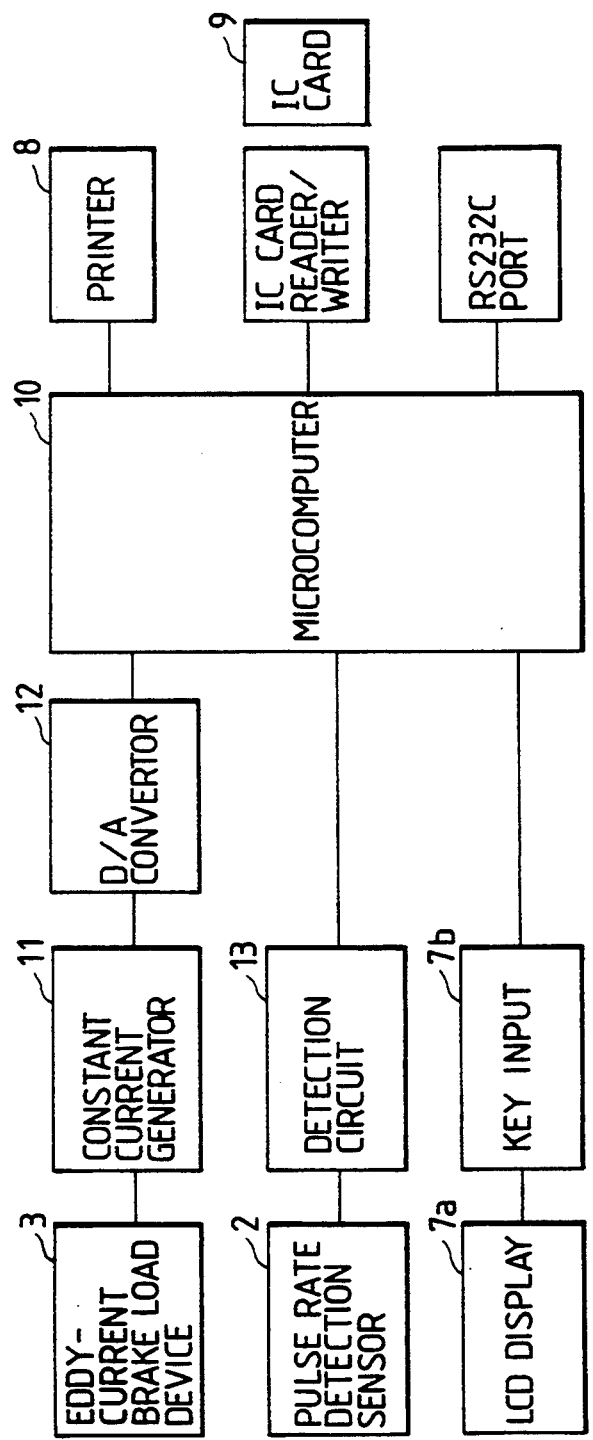
FIG. 6 is a block diagram illustrating the configuration of the control box of the measurement apparatus of the preferred embodiment.

FIG. 6 is a block diagram of the control circuit of the control box 7. A microcomputer 10 executes the main function of the control box 7. First, the microcomputer 10 decides what ramp load to generate in accordance with data of the state of the load, age, weight, sex and any other variables inputted through the function keys 7b, or such data received from the memory card 9, or the like. Based on the load of the eddy-current brake load device 3 outputted as load data through a constant-current regulated power source 11 and a D/A converter 12, and the output (photoelectric conversion data) of the pulse rate detection sensor 2 through a detection circuit 13 (photoelectric pulse-wave detection circuit in the case of photoelectric conversion data), the microcomputer 10 adjust a ramp load in accordance with a patient based on a predetermined program. Further, the microcomputer 10 calculates a measurement continuing time from the above-mentioned input data (particularly age and sex). The measurement time allows the value of the patient's pulse rate to reach 75% of estimated HRmax. To calculate this measurement continuing time, as a reference of the estimated maximum heart rate (HRmax) of a Japanese subject, a generally known value of HRmax=209−0.69·age [male], HRmax=205−0.75·age [female], or HRmax=220−age [general], or the like is used, and 75% HRmax is used as a condition of ending the exercise, so that the oxygen uptake measured at the point of time of ending the exercise is displayed as an evaluation of the patient's physical strength. However, any appropriate method can be used for estimating HRmax.

To measure physical strength, a subject places the pulse rate detection sensor 2 on an appropriate body portion and rides on the bicycle ergometer 1. Then the subject sets the memory card 9 or operates the function keys 7b to thereby input age, weight and sex so that the size of a ramp load is set to, for example, "male: 15 W/min, female: 10 W/min" automatically. The load is increased gradually after a program starts, and the value of pulse rate (or heart rate) is measured at every heart beat during the measurement. Further, the measurement may be carried out while measuring blood pressure by means of a blood pressure measuring device during the measurement to ensure safety.

A method of measuring physical strength by using the above-mentioned apparatus for measuring physical strength will be described following the procedure outlined below.

(1) A subject rides on the saddle 5 and puts the pulse rate detection sensor 2 (refer to FIG. 5) on an earlobe.

(2) The subject rests for one minute.

(3) The subject pedals at the pedal rotating speed of 50 rpm with no applied load for one minute in order to stabilize the response of pulse rate.

When the above preparations are completed:

(4) Keeping the pedal rotating speed at 50 rpm, the subject pedals under a ramp load (male: 15 W/min, female: 10 W/min) till their pulse corresponds to 75% HRmax.

Figure 7:
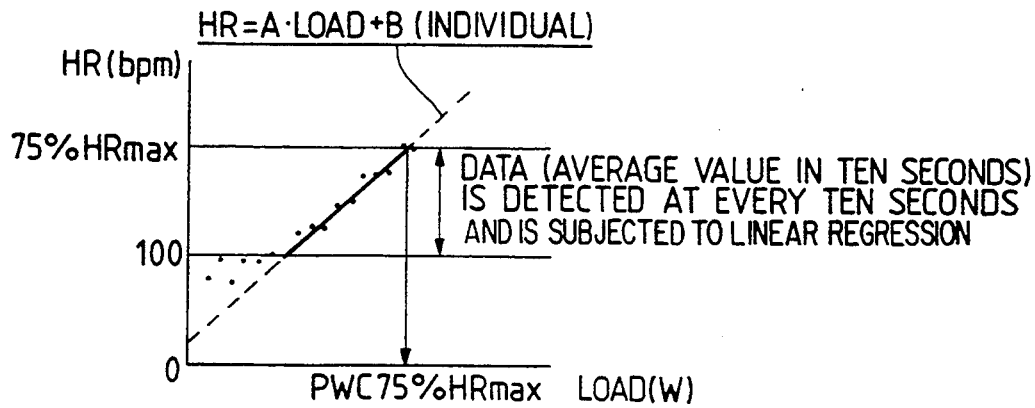
FIG. 7 is a load versus heart rate straight line diagram for explaining the method of measuring physical strength according to the preferred embodiment.
Figure 8:
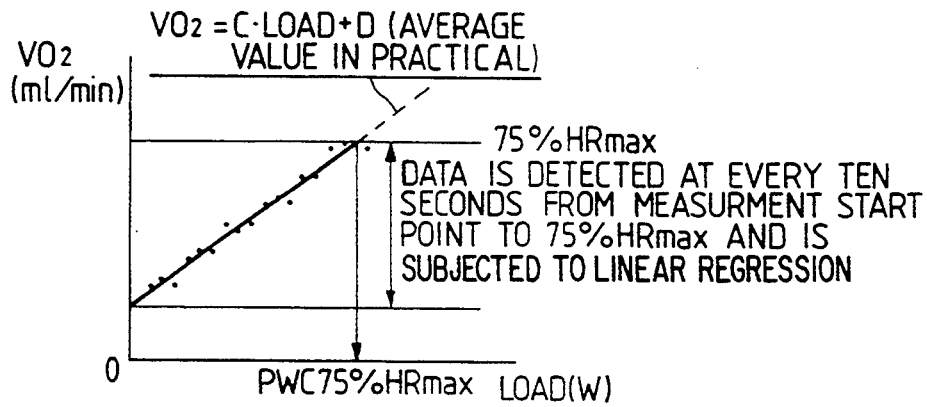
FIG. 8 is a load versus oxygen uptake rate straight line diagram for explaining the method of measuring physical strength according to the preferred embodiment.
Figure 9:
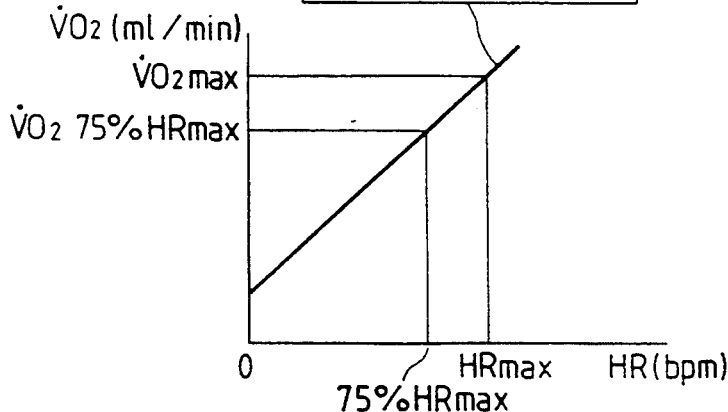
FIG. 9 is a $VO_2$@75% HRmax estimated straight line diagram for explaining the method of measuring physical strength according to the preferred embodiment.

(5) Pulse rates and load values are averaged in the range of from 100 bpm (beats per minute) to 75% HRmax for every 10 seconds and the plotted data curve is subjected to regression to obtain a straight line $HR = (A \cdot W) + B$, wherein W is the load (see FIG. 7).

(6) C and D are determined by an average regression straight line of $VO_2 = C \cdot W + D$ which has been determined in advance separately for males and females based on test data for several subjects (see FIG. 8), and A and B obtained through the measurement in the above item (5) are substituted in the estimation expression to eliminate the term W resulting in $VO_2 = (C/A) \cdot HR + [D - (B \cdot C)/A]$ (see FIG. 9), and further 75% HRmax is substituted as the heart rate (HR) to thereby obtain $VO_2$ which corresponds to an estimated value of VO_2@75% HRmax (See to FIGS. 7 to 9), wherein $VO_2$ is the volume of oxygen uptake per minute. VO2@75% HRmax thus estimated or measured is used as an evaluation of physical strength and compared with an evaluation table, made up of data from many subjects measured in advance, to thereby evaluate the physical strength of the subject.

(7) The above evaluation is output to a printer, an IC card, an external output RS232C port, or the like.

Figure 10:
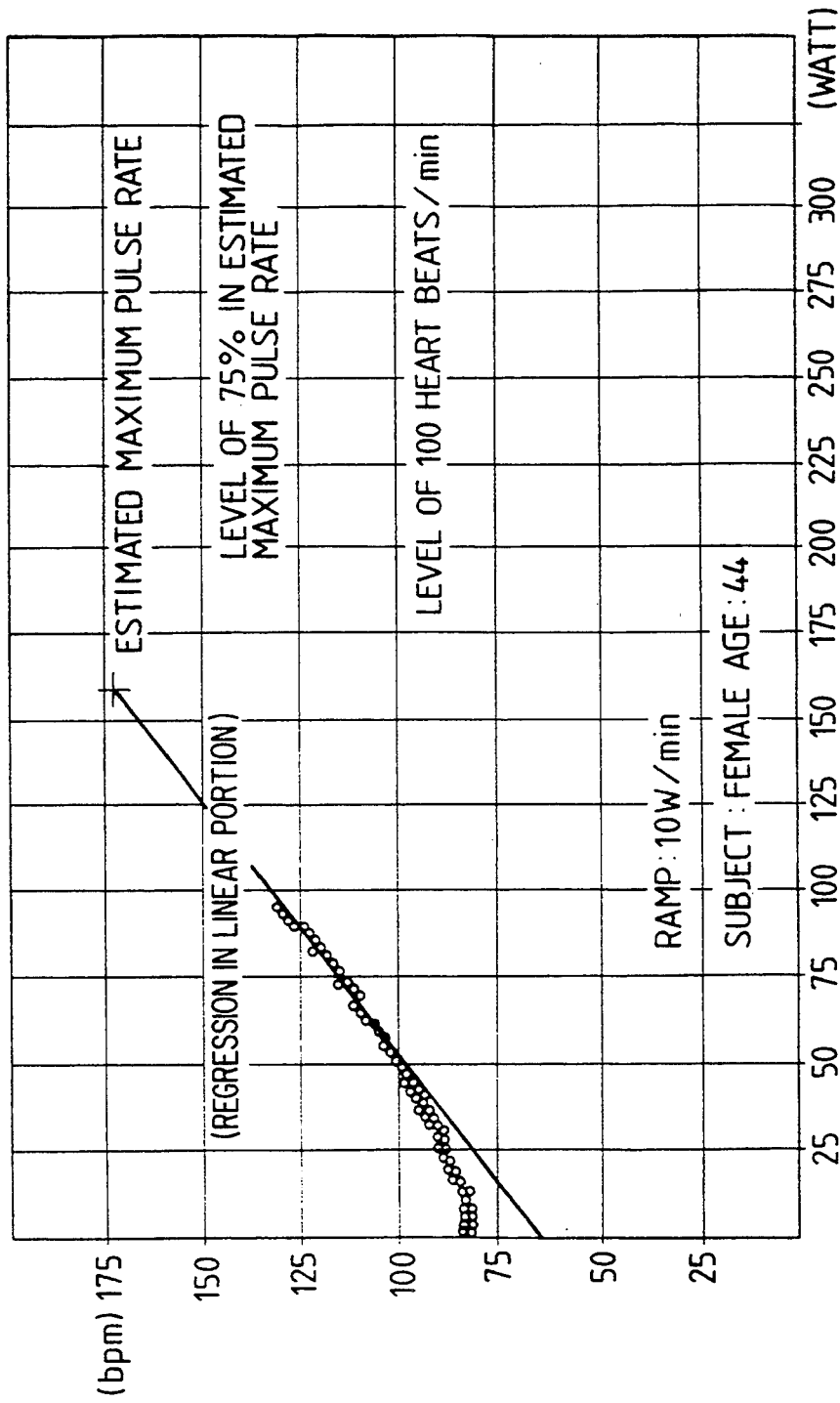
FIG. 10 is a load versus pulse rate curve diagram measured with a ramp load by using the apparatus for measuring physical strength according to the preferred embodiment.

FIG. 10 shows data illustrating that the increase of the cardiac stroke volume saturates at rates over 100 bpm. Measuring data in this range thus improves the accuracy of measurement for estimation.

Figure 11:
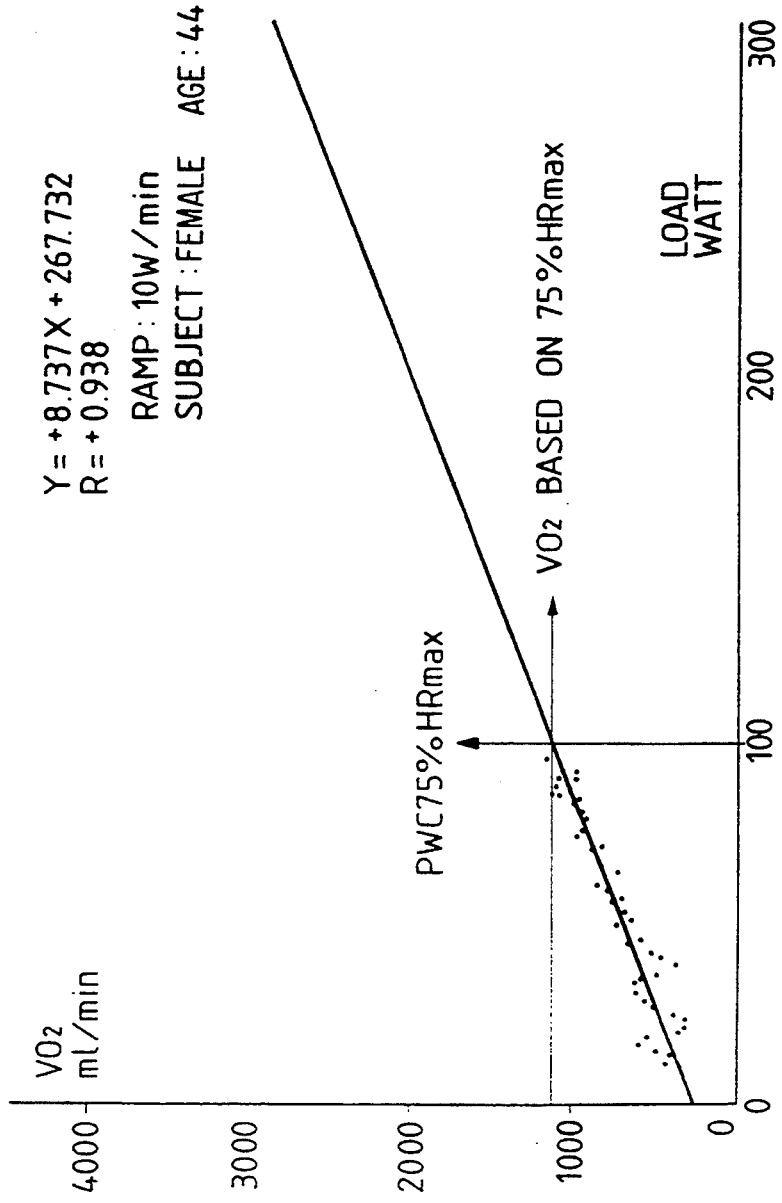
FIG. 11 is a load versus oxygen uptake rate straight line diagram measured with a ramp load by using the apparatus for measuring physical strength according to the preferred embodiment.

FIG. 11 shows that it is necessary in practice to utilize regression in the case of obtaining a measured oxygen uptake relative to a load since actual momentary or averaged measured values of oxygen uptake may be scattered about a straight line. In addition, one minute at the leading edge of momentary values of oxygen uptake during a ramp load is excluded from the regression since the delayed response of the patient's body may deteriorate the data in the first minute.

Figure 12:
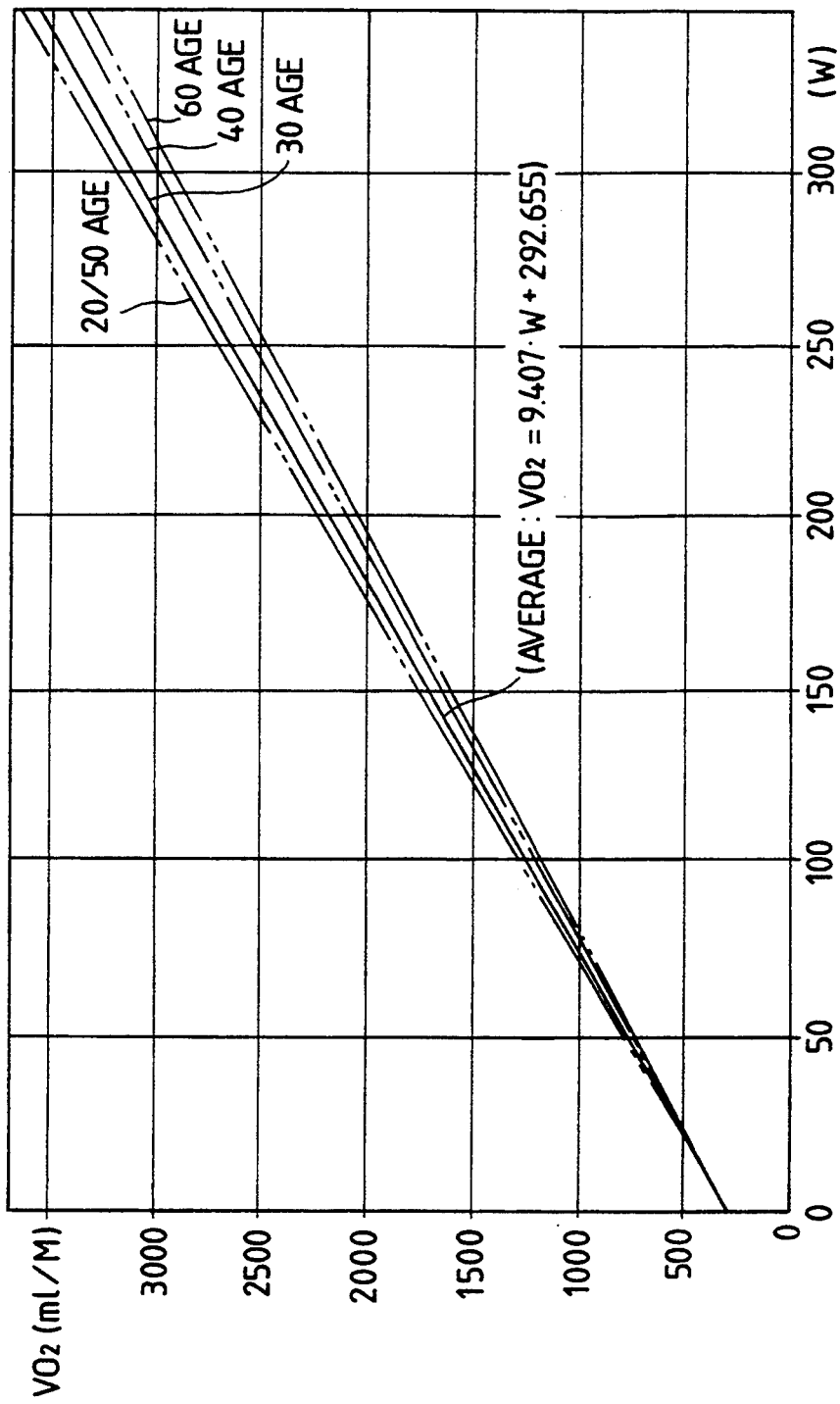
FIG. 12 is a load versus oxygen uptake rate straight line diagram measured for males of various ages by using the apparatus for measuring physical strength according to the preferred embodiment.
Figure 13:
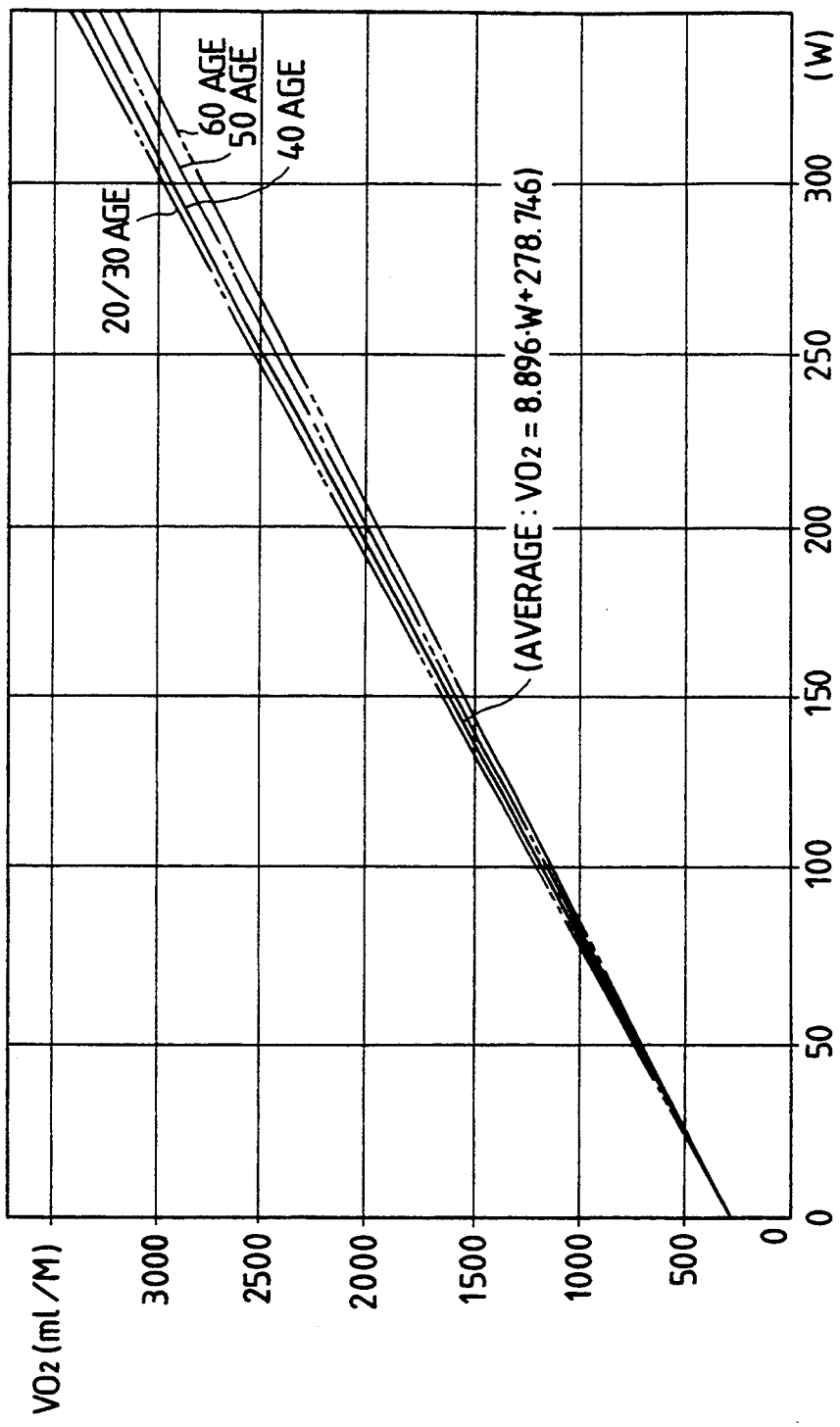
FIG. 13 is a load versus oxygen uptake rate straight line diagram measured for females of all ages by using the apparatus for measuring physical strength according to the preferred embodiment.

FIGS. 12 and 13 show an average W − VO$_2$ straight line for every age in each sex and an average W − VO$_2$ straight line for each sex calculated based on known equations. The gradient and segment of such an average line are respectively used as C and D for estimation.

Figure 14:
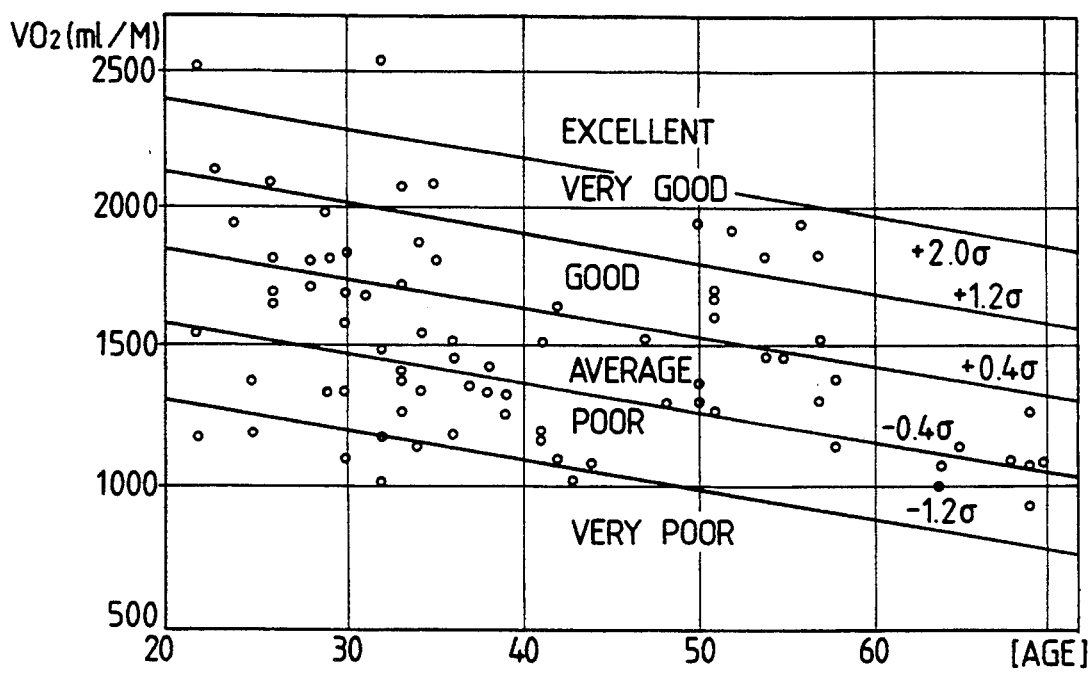
FIG. 14 is a physical strength evaluation table for males based on 75% HRmax and measured by using the apparatus for measuring physical strength according to the preferred embodiment.
Figure 15:
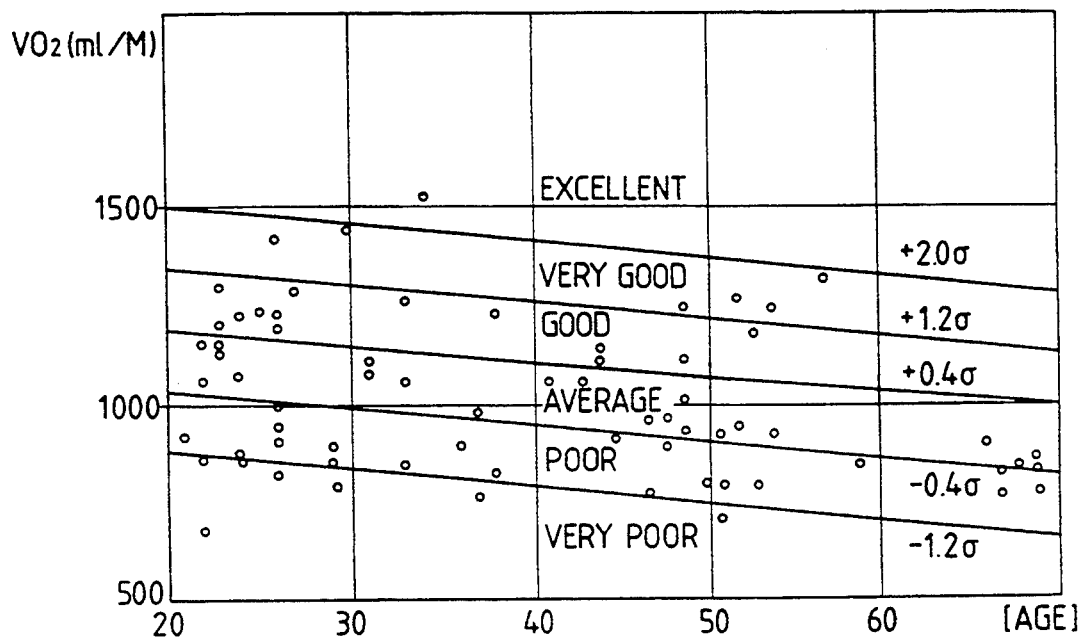
FIG. 15 is a physical strength evaluation table for females based on 75% HRmax and measured by using the apparatus for measuring physical strength according to the preferred embodiment.

FIGS. 14 and 15 are evaluation tables respectively for males and females based on measured values of VO$_2$@75% HRmax. An aging phenomenon in the significant level 1% has been confirmed.

Figure 16:
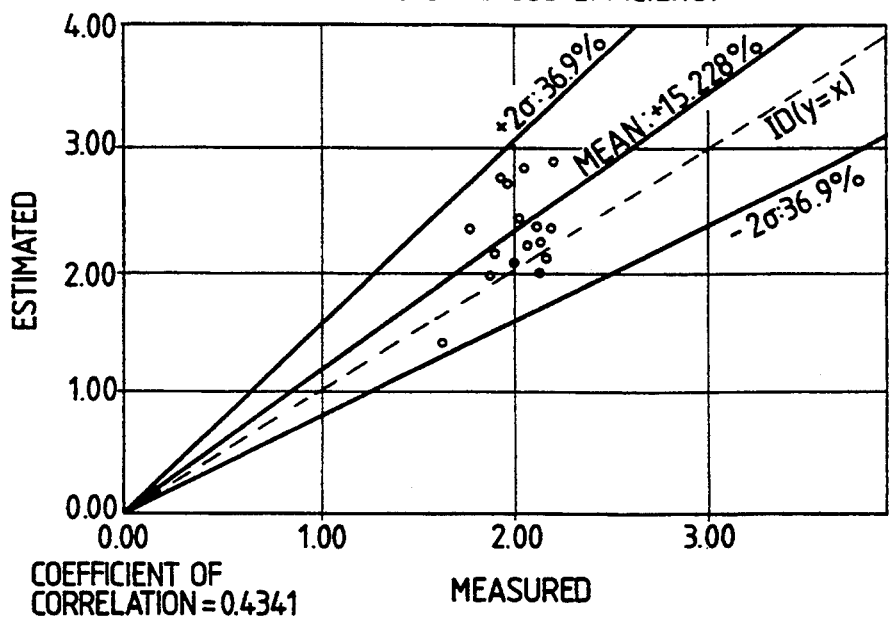
FIG. 16 is an error table between maximum oxygen uptake measured by using the apparatus for measuring physical strength according to the preferred embodiment, and maximum oxygen uptake estimated in accordance with a gross system.

FIG. 16 shows the result obtained through comparison between the actual measurement of the maximum oxygen uptake, in order to confirm the accuracy of estimation, and the estimation obtained by using a conventional method of using gross efficiency (a method of estimating VO$_2$ by VO$_2$=(efficiency)·(scale factor)·W provided the efficiency of the bicycle ergometer is 23.3%; see "Introduction of Exercise Physiology", published by Taishukan Shoten, pp. 168 to 173).

Error was defined by the following expression in order to confirm the accuracy.

$$\text{error} = \frac{\text{estimated value} - \text{measured value}}{\text{measured value}} \cdot 100\%$$

As a result, the average of errors was 15.228% from the ID line, and the dispersion of the errors was 36.9% expressed by a double of the standard deviation. It is understood that the errors were large and were apt to make estimated values high on the average.

Figure 17:
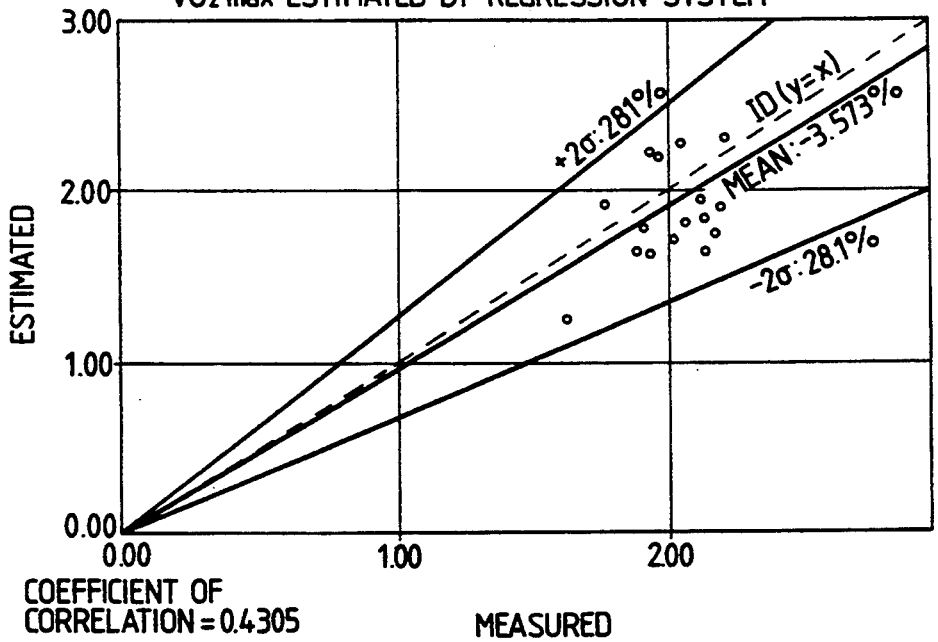
FIG. 17 is an error table between maximum oxygen uptake measured by using the apparatus for measuring physical strength according to the preferred embodiment, and maximum oxygen uptake estimated in accordance with a regression system.

FIG. 17 shows the result of confirmation of the accuracy in estimation of the maximum oxygen uptake in the same manner as the present invention. It is understood that the dispersion of errors were not changed significantly. However, the average of the errors was significantly closer to the ID line.

Figure 18:
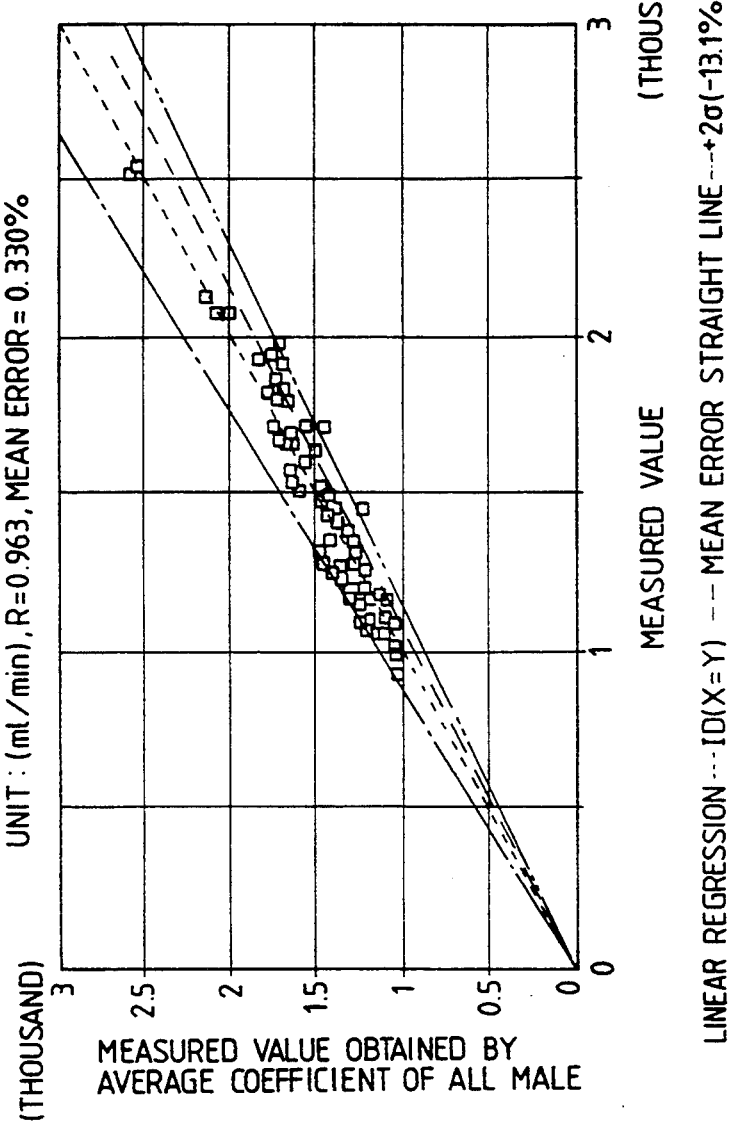
FIG. 18 is a diagram of a relationship between estimated values and measured values of a oxygen uptake @75% HRmax of all males measured by using the apparatus for measuring physical strength according to the preferred embodiment.

FIGS. 18 and 19 show the result of estimation according to the present invention, and in spite of measurement on subject's ranging in age from their twenties to their sixties, the following result was obtained and the accuracy of estimation was improved over known methods.

Male: mean error: 0.33% dispersion±13.1%

Female: mean error: 0.262% dispersion±16.9%

As has been described, according to the present invention, measurement can be safely performed upon middle and high ages in accordance with the index of VO$_2$@75% HRmax of maximum heart rate with which measurement can be estimated, and the measurement can be used for general purposes because an estimated value of oxygen uptake is used for evaluating physical strength and the estimated value is not dependent on the particular apparatus. Particularly, the estimated value can always be compared with a measured value. Therefore the accuracy of the measurement apparatus can be shown clearly. In addition, 75% of maximum heart rate is significant in exercise physiology as an upper limit of aerobic oxygen exercise, and it can be compared in relation to a PWC75% HRmax evaluation which is used broadly, so that it is possible to provide a method of evaluating general endurance of older patients.

What is claimed is:

1. A method of measuring the physical strength of a subject comprising the steps of:

exercising said subject for a period of time thereby increasing a heart rate of said subject terminating said exercise when the heart rate of the subject has reached 75% of the subject's maximum heart rate HRmax;

measuring oxygen uptake after terminating the exercise period; and evaluating said measured oxygen uptake as a physical strength indicator.

2. A method as recited in claim 1, further comprising:

determining the maximum heart rate HRmax based on the relationship, HRmax=209−(0.69×age) when the subject is male and the relationship HRmax=205−(0.75×age) when the subject is female, age being the subject's age.

3. A method as claimed in claim 1, further comprising:

determining the maximum heart rate HRmax based on the relationship, HRmax=220−age, age being the subject's age.

4. A method as claimed in claim 1, further comprising:

exercising the subject using a bicycle ergometer having an increasing ramp load; and setting a rate of said ramp load so that the heart rate of the subject reaches 75% of the subject's maximum heart rate HRmax in about 10 minutes.

5. A method as claimed in claim 4, further comprising:

setting said ramp load to 15 W/min for a male subject and 10 W/min for a female subject.

6. A method of estimating physical strength of an individual subject comprising the steps of:

applying an increasing load to a plurality of male and female subjects;

measuring oxygen uptake, VO$_2$, of said male and female subjects while applying said load and generating oxygen uptake data;

collecting said oxygen uptake data indicating oxygen uptake relative to said load value;

subjecting said oxygen uptake data to regression to obtain a straight line (W− VO$_2$ straight line) while excluding oxygen uptake data obtained within one minute from a start of measurement;

applying a ramp load to said individual subject;

measuring a heart rate of said individual subject while applying said ramp load to obtain a load value, PWC75% HRmax, when the heart rate reaches 75% of the subject's maximum heart rate;

substituting PWC75% HRmax as a load value into said obtained straight line, and determining an actual value of VO$_2$@75% HRmax (oxygen uptake when the heart rate reaches 75% of estimated maximum heart rate) as a physical strength indicator.

7. A method of estimating physical strength of an individual subject comprising the steps of:

applying an increasing load to a plurality of male and female subjects:

measuring oxygen uptake, VO$_2$, of said male and female subjects while applying said load and collecting oxygen uptake data;

subjecting said oxygen uptake data to linear regression to determine the relationship $VO_2 = C*W + D$, between oxygen uptake, VO₂, and a load W, where C is a determined slope and D is a determined offset; and estimating oxygen uptake at 75% of a maximum heart rate of the individual subject as a strength indicator using said determined slope C and said determined offset D.

8. A method as claimed in claim 7, wherein said step of subjecting said oxygen uptake data to linear regression further comprises:

excluding oxygen uptake data collected during a first minute of application of said load.

9. A method of estimating physical strength comprising the steps of:

applying an increasing ramp load to a subject;

measuring a heart rate of said subject while applying said ramp load to obtain heart rate data while said heart rate is greater than 100 beats per minute and not greater than 75% of a maximum heart rate of said subject;

subjecting said heart rate data to linear regression to obtain the relationship $$HR = A*W + B,$$

where HR is heart rate, A is a determined slope, W is a load and B is a determined offset; and estimating physical strength of the subject using said determined slope A and said determined offset B.

10. A method of estimating physical strength of an individual subject comprising the steps of:

applying an increasing load to a plurality of male and female subjects;

measuring oxygen uptake, VO₂, of said male and female subjects while applying said load and collecting oxygen uptake data;

subjecting said oxygen uptake data to linear regression to determine the relationship $$VO_2 = C*W + D,$$

between oxygen uptake, VO₂, and a load W, where C is a first determined slope and D is a first determined offset;

applying a ramp load to said individual subject;

measuring a heart rate of said individual subject while applying said ramp load to obtain heart rate data while said heart rate is greater than 100 beats per minute and not greater than 75% of a maximum heart rate of said individual subject;

subjecting said heart rate data to linear regression to obtain the relationship $$HR = A*W + B,$$

where HR is heart rate, A is a second determined slope, W is a load and B is a second determined offset; and estimating an oxygen uptake, VO₂, of said individual subject as a physical strength indicator by substituting a value equal to 75% of the individual subject's maximum heart rate for HR in the following expression:

$$VO_2 = C/A*HR + [D - (B*C)/A].$$

11. A method as claimed in claim 10, wherein said step of subjecting said oxygen uptake data to linear regression further comprises:

excluding oxygen uptake data collected during a first minute of application of said load.

12. An apparatus for estimating physical strength of an individual subject during an exercise period, comprising:

an input device receiving input data regarding at least one of said subject's age, sex and weight;

a storage device storing data regarding W − VO₂ (load versus oxygen uptake) for a plurality of male and female subjects separately;

a pulse rate detector measuring a pulse rate of said individual subject and outputting pulse rate data;

a bicycle ergometer having an electro-magnetic eddy-current brake configured to apply a linearally increasing load to said subject, said load being based on an electrical signal applied to said electro-magnetic brake;

a micro-processor collecting said pulse rate data from said pulse rate detector, receiving input data from said input device and data regarding W − VO₂ from said storage device and providing said electrical signal to said electro-magnetic brake; and a display device connected to said micro-processor;

wherein said micro-processor determines an estimate of the subject's physical strength based on said collected pulse rate data, said received data from said input device and said stored data regarding W- VO₂ (load versus oxygen uptake) for male and female subjects separately and displays said determined estimate of physical strength on said display device.

13. An apparatus as claimed in claim 12, wherein said signal provided to said bicycle ergometer by said micro-processor causes the brake to apply the load at an increasing rate of 15 W/minute for a male subject and 10 W/minute for a female subject during said exercise period.

* * * * *